(12) United States Patent
Vogl

(10) Patent No.: US 9,347,870 B2
(45) Date of Patent: May 24, 2016

(54) DEVICE FOR PHOTOMETRICALLY OR SPECTROMETRICALLY EXAMINING A LIQUID SAMPLE

(75) Inventor: Wolfgang Vogl, Zwerndorf (AT)

(73) Assignee: VWM GMBH, Zwerndorf (Weiden A. D. March) (AT)

( * ) Notice: Subject to any disclaimer, the term of this patent is extended or adjusted under 35 U.S.C. 154(b) by 0 days.

(21) Appl. No.: 13/993,372

(22) PCT Filed: Dec. 15, 2011

(86) PCT No.: PCT/AT2011/000497
§ 371 (c)(1),
(2), (4) Date: Jun. 12, 2013

(87) PCT Pub. No.: WO2012/079103
PCT Pub. Date: Jun. 21, 2012

(65) Prior Publication Data
US 2013/0265580 A1 Oct. 10, 2013

(30) Foreign Application Priority Data
Dec. 15, 2010 (AT) ................................. A 2077/2010

(51) Int. Cl.
*G01N 21/00* (2006.01)
*G01N 21/03* (2006.01)
*G01N 21/05* (2006.01)

(52) U.S. Cl.
CPC ............ *G01N 21/0303* (2013.01); *G01N 21/05* (2013.01); *G01N 2021/0378* (2013.01); *G01N 2021/0392* (2013.01); *G01N 2021/054* (2013.01)

(58) Field of Classification Search
USPC .............. 356/432–442, 39–40, 246, 335–343
See application file for complete search history.

(56) References Cited

U.S. PATENT DOCUMENTS 2,592,329 A * 4/1952 Schlumberger et al. ...... 356/154
4,654,535 A * 3/1987 Wolske .......................... 250/577
(Continued)

FOREIGN PATENT DOCUMENTS

DE       4336520 A1    4/1995
DE   102006052887 A1    5/2008
(Continued)

OTHER PUBLICATIONS

English Abstract of JP H10-104153 published Apr. 24, 1998.
(Continued)

*Primary Examiner* — Tri T Ton
(74) *Attorney, Agent, or Firm* — Nevrivy Patent Law Group P.L.L.C.

(57) ABSTRACT

The invention relates to a device (1) for photometrically or spectrometrically examining a liquid sample (2), comprising a cuvette (3, 3'), which can be arranged in the beam path between a radiation source (4) and a radiation detector (5) and which accommodates the liquid sample (2) to be examined, a radiolucent inlet section (6) for coupling in radiation (20) produced by means of the radiation source (4), which radiation interacts with a sample volume (8), and a radiolucent outlet section (7) for coupling out radiation (20") intended to be detected in the radiation detector (5), wherein the inlet section (6) has an inlet surface (11) convexly curved in such a way and/or the outlet section (7) has an outlet surface (12, 12') spherically convexly curved in such a way that the incident radiation (20, 20') is focused in the manner of a converging lens.

14 Claims, 4 Drawing Sheets

(56) References Cited

U.S. PATENT DOCUMENTS

| | | | |
|---|---|---|---|
| 4,886,356 | A | 12/1989 | Paradis |
| 7,262,847 | B2 * | 8/2007 | Goodall et al. ............... 356/344 |
| 2002/0080349 | A1 * | 6/2002 | Armstrong et al. ........... 356/246 |
| 2003/0103204 | A1 | 6/2003 | Kerstan et al. |

FOREIGN PATENT DOCUMENTS

| | | |
|---|---|---|
| EP | 0404258 A2 | 12/1990 |
| EP | 0798551 A2 | 10/1997 |
| EP | 0542487 | 9/1998 |
| JP | H01-109245 | 4/1989 |
| JP | H02-042337 | 2/1990 |
| JP | H06-123698 | 5/1994 |
| JP | 3036930 | 2/1997 |
| JP | H09-264840 | 10/1997 |
| JP | H10-104153 | 4/1998 |
| JP | 2006-189292 | 7/2006 |
| JP | 2007-086036 | 4/2007 |
| JP | 2010-185705 | 8/2010 |
| RU | 2343456 | 1/2009 |
| WO | 2006/035012 | 4/2006 |

OTHER PUBLICATIONS

English Abstract of JP 2006-189292 published Jul. 20, 2006.
English Abstract of JP H02-042337 published Feb. 13, 1990.
English Abstract of JP H09-264840 published Oct. 7, 1997.
English Abstract of JP 2007-086036 published Apr. 5, 2007.
English Abstract of JP H06-123698 published May 6, 1994.
English Abstract of JP 2010-185705 published Aug. 20, 2010.
English Abstract of JP H01-109245 published Apr. 26, 1989.
Office Action dated Aug. 25, 2015 in corresponding application JP 2013-543465.
English translation of Office Action dated Aug. 25, 2015 in corresponding application JP 2013-543465.
Office Action in corresponding application RU 2013126559/28(039408) dated Nov. 5, 2015.
English language translation of the Office Action in corresponding application RU 2013126559/28(039408) dated Nov. 5, 2015.
English language translation of Office Action in corresponding application CN 201180060724.X dated Jan. 15, 2016.

* cited by examiner

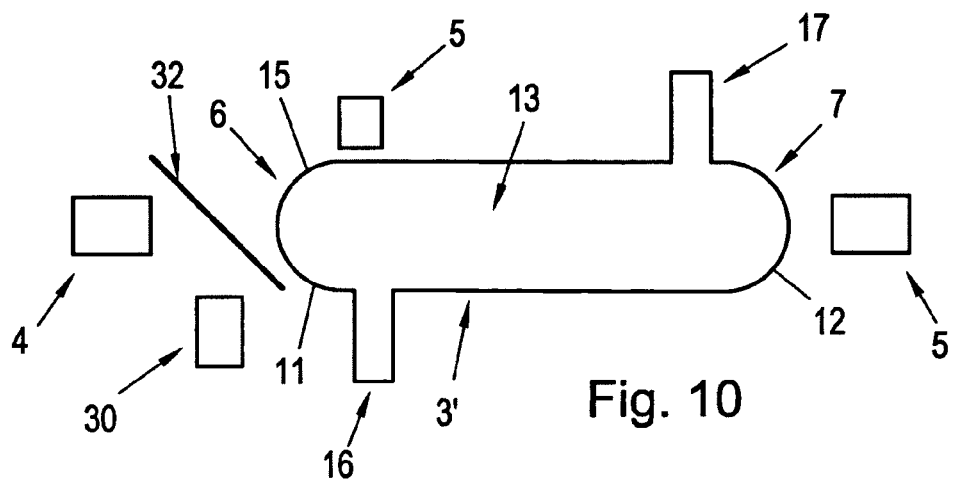
Fig. 10
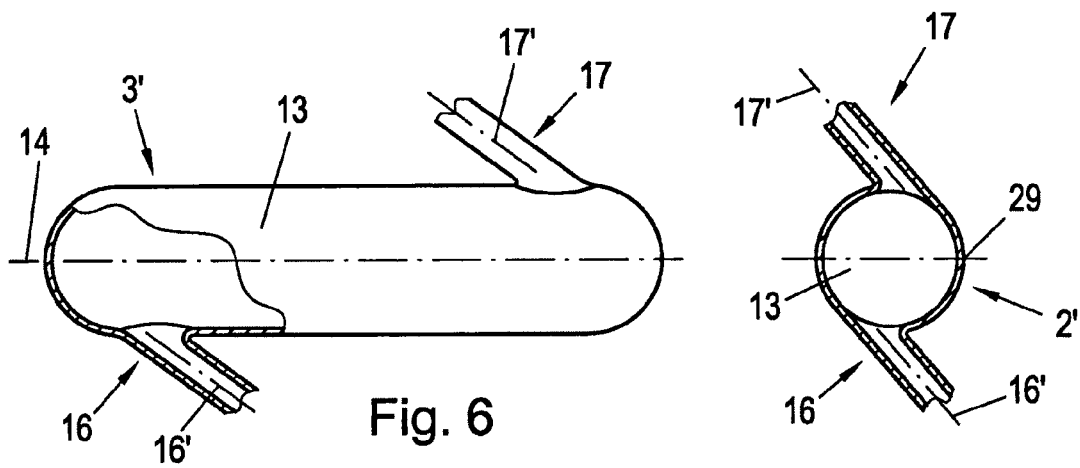
Fig. 6
Fig. 7
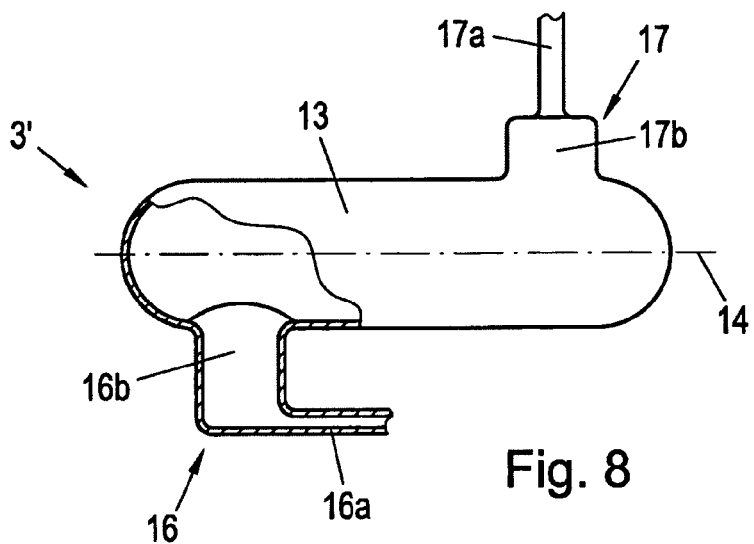
Fig. 8

DEVICE FOR PHOTOMETRICALLY OR SPECTROMETRICALLY EXAMINING A LIQUID SAMPLE

FIELD OF THE INVENTION

The invention relates to a device for photometrically or spectrometrically examining a liquid sample, comprising a cuvette, which can be arranged in the beam path between a radiation source and a radiaton detector and which accommodates the liquid sample to be examined, a radiolucent inlet section for coupling in radiation produced by means of the radiation source, which radiation interacts with a sample volume, and a radiolucent outlet section for coupling out radiation intended to be detected in the radiation detector.

BACKGROUND INFORMATION

Such devices are employed for conducting analytical methods in order to qualitatively and quantitatively detect chemical parameters of liquid samples. The cuvette constitutes a liquid cell which accommodates the liquid sample to be examined. The sample is reacted with an adequate reagent in order to induce changes in the optical properties of the solution which may be measured photometrically. For this purpose, a radiation source is provided which produces visible light, infrared light or ultraviolet light, depending on the application. The cuvette displays an inlet window which is transparent to the employed excitation radiation for coupling in the excitation radiation which, after having passed through the sample volume, is coupled out via the outlet window. Hitherto, cuvette tests or equivalent tests have usually been performed using cuvettes with plane-parallel walls displaying incorporated inlet and outlet windows. Additionally, a lens system is provided in many cases in order to achieve an appropriate beam deflection or beam transformation on its way from the radiation source to the detector.

In the context of a transmitted light refractometer, the practice of arranging a hollow cuvette in the telecentric beam path of a monochromatic light source generating a divergent beam bundle, which is formed into a parallel beam bundle by means of a condenser and is focused, after having passed through the cuvette, onto a line-shaped sensor by means of a lens, has been known from DE 42 23 480 A1, for example. Such devices allow for precise deflection and imaging of the radiation to be examined, which is specifically adapted to the respective application. Disadvantageously, such imaging systems are very cost-intensive; furthermore, installing and adjusting the optical system is difficult and can often only be performed by a person with the necessary technical skill. Moreover, a great number of transition areas and interfaces are involved, causing imaging errors and performance loss.

In another context, DE 38 35 347 A1 describes a liquid cell having semicircular ends which is employed for laser intensification or phase conjugation by utilizing stimulated scattering processes.

Further, different types of turbidity sensors are known from DE 10 2006 052 887 A1, EP 0 404 258 A2 and DE 43 36 520 A1.

SUMMARY OF THE INVENTION

By way of contrast, the object of the present invention is to create a constructionally simple, cost effectively producible device of the initially described kind, which enables precise imaging of the excitation radiation used for examining the liquid sample and is easy to install and adjust.

This object is established in the device of the initially described kind by an inlet section having an inlet surface convexly curved in such a way and/or an outlet section having an outlet surface spherically convexly curved in such a way that the incident radiation is focused in the manner of a converging lens.

Accordingly, at least one of the cuvette surfaces intended for coupling in or coupling out radiation is convexly curved so that the incident radiation can be focused, i.e. the beam expansion can be reduced. In this way, the cuvette directly assumes tasks of the optical system which has hitherto been functionally and constructively separated from the cuvette. By having essential elements of beam formation integrated into the cuvette, a compact, cost effective photometric device may be provided which may be easily set up and positioned in the beam path between the radiation source and the radiation detector. Thus, installation expenditure is reduced considerably; furthermore, adjustment is substantially easier compared to conventional devices with separate optical systems. The number of transition areas is substantially lower than with external optical systems so that imaging errors and performance losses may be minimized. The device is thus particularly suited for photometric or spectrometric examinations which need to be performed quickly and cost effectively, do not require a sophisticated high-quality optical system but need to be as simple as possible to operate. Preferably, both the inlet surface and the outlet surface are convexly curved so that in combination the effect of a biconvex converging lens is achieved. Depending on the application, it is, however, imaginable for either the inlet surface or the outlet surface to be convexly curved; this configuration is then comparable to a plane-convex converging lens. Of course, it is not intended that the invention be limited to cuvettes having only one inlet or outlet surface; in particular, it is often desirable to couple out the beam bundle at more than one outlet sections in order to gain additional information on the radiation interacting with the sample volume. The convexly curved inlet and/or outlet surface may extend along the entire inlet or outlet section of the cuvette; it is, however, conceivable to have an inlet and/or outlet section which is convexly curved only in some parts. Preferably, the inlet and/or outlet sections have coatings, each of which is expediently formed by a λ/4-layer. In order to expediently form a beam, the inlet surface and/or outlet surface are essentially spherically curved in the area of the cuvette interfaces intended for coupling in or coupling out radiation. Constructing the optically active surfaces, i.e. the inlet and/or outlet surfaces, in the shape of spherically curved surfaces is preferred from a manufacturing point of view; it is also conceivable to construct the inlet and/or outlet surface with a slightly aspherical curve, i.e. in a rotationally symmetrical form, which, in contrast to exactly spherical surfaces, does not equate to a section of a spherical surface. The additional degrees of freedom of spherical lenses may be used to reduce imaging errors which are inevitable with exactly spherical surfaces.

In a first preferred embodiment a cuvette comprises a liquid cell through which radiation passes essentially along the cell's longitudinal axis and which, in particular, is of a substantially cylindrical shape, wherein an end surface of the liquid cell is formed as a convexly curved inlet surface or outlet surface. The end surfaces of the cuvette are, in particular, arranged essentially transversely to the longitudinal axis of the cuvette. If both end surfaces are convexly curved, radiation can be made to pass conveniently through the liquid sample. This embodiment is advantageous in that the radiation in the cuvette passes through a relatively long distance, making for a large interacting volume and enabling highly accurate examination of the chemical parameters, for example the concentration of a certain solution component. Expediently, the end surfaces of the, in particular, substantially cylindrical liquid cell are curved such that the excitation radiation is focused into an essentially parallel beam bundle along the longitudinal axis of the cuvette, said beam passing essentially completely through the solution contained in the liquid cell.

In another preferred embodiment it is of advantage if the cuvette comprises a liquid cell through which radiation passes essentially transversely to the cell's longitudinal axis and which, in particular, is of a substantially cylindrical shape, wherein the convexly curved inlet surface and/or outlet surface are formed on the cell's lateral surfaces. In this embodiment, accordingly, inlet and outlet surfaces are provided which curve convexly, i.e. outwardly from the lateral surfaces of the liquid cell.

If the cuvette is designed as a flow through cuvette which has a supply line and a discharge line for the liquid sample under examination, then the chemical or physical processes may be examined continuously. This, in particular, enables continuous detection of changes in the chemical parameters, such as concentrations.

To avoid air inclusions in the liquid sample it is favorable if, with respect to the cuvette's operating position, the supply line is connected to the cuvette vertically below the discharge line, wherein the discharge line is preferably connected to an upper-side section of the cuvette. Accordingly, the liquid sample is supplied from below and is discharged from further above, reliably preventing, or at least considerably reducing, air bubble formation which may interfere with the examination. For this purpose, it is particularly favorable to connect the discharge line to the upper side of the cuvette such that the liquid sample is discharged upwards from the uppermost point.

With respect to improved blending of the liquid sample and favorable flow conditions, it is of advantage that a longitudinal axis of the supply line and/or a longitudinal axis of the discharge line be inclined relative to a longitudinal axis and/or a transverse axis of the flow through cuvette.

In an alternative embodiment of the flow through cuvette, improved flow conditions may be achieved by using a supply line and/or discharge line exhibiting sections with different cross sectional areas.

For many applications, in particular flow through cytometry and related measuring procedures, it is of advantage if the cuvette exhibits at least one convexly curved outlet surface for a forwardly scattered beam bundle and another convexly curved outlet surface for a transversely scattered beam bundle. Flow through cytometry relies on the emission of optical radiation of a cell which is subjected to radiation of a high intensity produced, for example, by a laser beam source. The scattered light is indicative of the size and form of the cell. The forward scatter light (FSC), i.e. the light diffracted at small angles, depends particularly on the cell volume. The beam bundle scattered in transverse direction, usually referred to as sideward scatter light (SSC), mainly provides information as to the granularity, size and structure of the cell or of cell components. Comparing forward scatter light and sideward scatter light to each other enables a differentiation of various blood cells, for example. In order to conduct flow through cytometry, it is favorable if the cuvette has a narrow channel through which the cell suspension is passed in a very thin spurt.

The invention further relates to a device comprising a radiation source configured in particular to produce a divergent beam bundle, which preferably is a light emitting diode (LED), and a radiation detector, preferably a CCD sensor ("charge coupled device"). Depending on the application, other types of radiation source, in particular a continuous radiation source, may of course be provided as well; if a high intensity is required, then in particular a laser source may be employed. However, the use of light emitting diodes is preferred in many cases as these constitute a very cost effective variant which is generally available for most of the wavelength ranges. A CCD camera is preferably equipped to detect transmitted radiation containing information on the liquid sample essentially along the entire length of the cuvette.

Expediently, a reference sensor is provided in order to calibrate the radiation detector.

According to a preferred embodiment, a stirring device for stirring the liquid sample is provided with which the liquid sample may be blended during the measurement. The stirring device is preferably configured as a magnetic stirrer.

For conducting photometric examinations at high measurement resolution, it is favorable if the convexly curved inlet surface focuses a beam bundle, in particular a divergent beam bundle, into a substantially parallel beam bundle, which, after having passed through the sample volume, is focused into a convergent beam bundle by means of the convexly curved outlet surface, which latter bundle is detectable by the radiation detector. In this way, radiation passes through a relatively large sample, thereby amplifying the measurement resolution, which depends on the sample volume. The lens system integrated into the cuvette makes it thus possible to specifically adapt the sample volume through which the radiation passes to the demands imposed on an analytical method, in particular with respect to the achievable resolution. In addition, the burden imposed on the sample by radiation may be reduced considerably if the radiation passes through a comparably large sample volume. This is highly important, in particular for the examination of organic samples by ultraviolet (UV) light, for example.

In a further preferred embodiment of the invention, an inlet surface of the cuvette is curved in such a way that the radiation impinging onto the inlet surface is focused within a relatively small focal area of the liquid sample; this is achieved by a relatively small radius of curvature of the inlet surface. In a constructionally simple manner, this design permits generation of a high energy density in the focal area of the liquid sample under examination. Provision of a high energy density is essential for many applications, for example in flow through cytometry. Thus, to energize a sample volume, radiation of relatively low intensity may be used, which is then focused by means of the inlet surface curved in the manner of a converging lens in order to achieve the required energy density in the sample volume. This permits the use of light emitting diodes as a radiation source, which have the advantage of low cost and availability for a wide range of wavelengths. The radius of curvature of the inlet surface is advantageously selected in line with the form and expansion of the incident radiation, which may be a divergent or parallel beam bundle.

BRIEF DESCRIPTION OF THE DRAWINGS

The invention is described in more detail below, with reference to preferred exemplary embodiments shown in the drawings. The invention is of course not limited to these embodiments. In detail, the drawing in:

FIG. 6 and FIG. 7 show a view of a flow through cuvette according to a further embodiment of the invention, which features an improved supply line and discharge line system with respect to the flow conditions;

FIG. 8 shows a view of a flow through cuvette, featuring an alternative supply line and discharge line system;

FIG. 10 shows a view of an alternative configuration for photometric or spectrometric examinations, comprising a translucent mirror.

DETAILED DESCRIPTION

Figure 1:
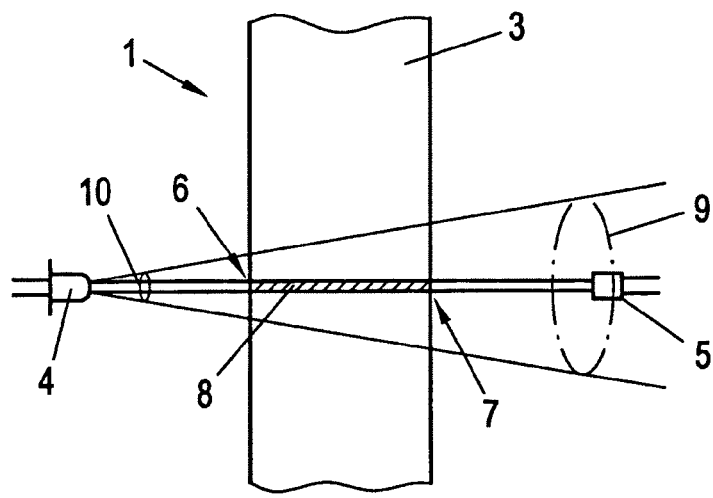
FIG. 1 shows a view of a device for photometrically or spectrometrically examining a liquid sample by means of a cuvette, wherein the inlet section and/or outlet section for excitation radiation are formed on plane-parallel lateral walls of the cuvette in accordance with the state of the art.

FIG. 1 shows a device 1, known from the state of the art, for photometrically determining a chemical parameter of a liquid sample 2, said device containing a solution to be examined, which is reacted with a suitable reagent in order to induce a modification of the optical properties of the solution which may be measured photometrically. The chemical parameter may be, for example, the concentration. Photometry relies on the measurement of the optical properties of radiation passing through the liquid sample 2. In a simple case, the absorption of the radiation may be used as a measure of the searched-for concentration of a solution component. In other cases, the scatter or diffraction ratio is detected. Alternatively, or in addition to photometrically examining the liquid sample 2, spectrometric measurements may be performed. Device 1 exhibits a cuvette 3, which is arranged between a radiation source 4 for generating radiation appropriate for photometric examination and a radiation detector 5 for detecting the transmitted radiation. Cuvette 3 displays an inlet section 6 on a wall directed towards the radiation source 4 for coupling in excitation radiation generated by means of the radiation source 4; in addition, an outlet section 7 is provided on an opposite wall of the cuvette 3, through which radiation interacting with a sample volume 8 of the liquid sample 2 is coupled out. The transmitted radiation impinges upon the radiation detector 5, which determines the searched-for chemical parameter of the liquid sample 2 from the measured physical quantity, in particular from the radiation intensity of the transmitted radiation. The cuvette 3 shown in FIG. 1 is configured with plane-parallel walls according to the state of the art. As is apparent from FIG. 1, only a very small sample volume 8 is measured by this cuvette 3; the main portion of the excitation radiation does not reach the radiation detector 5. FIG. 1, schematically delineates an illuminated area 9, which is many times greater than an excitation cross section 10 of the excitation radiation, which fans out continuously between radiation source 4 and radiation detector 5. Thus, only a fraction of the excitation energy is utilized for examining the liquid sample 2. The signal strength at the radiation detector 5 is determined essentially by the intensity of the excitation radiation and the ratio of the illuminated area 9 to the sensor surface. Thus, the shown configuration only produces a relatively low signal strength and a low resolution, which may in certain cases be unsufficient for determining low concentrations.

For this reason, complex lens systems (not shown in FIG. 1) are often used in the state of the art to provide for appropriate imaging of the excitation radiation, with the aim of magnifying the effective sample volume 8 to be examined or the signal impinging upon the radiation detector 5. However, additional optical components such as condenser or objective lenses, for example, are expensive to produce. Furthermore, adjusting these lenses is difficult as the lenses have to be positioned in precise alignment with the cuvette 3 in order to deflect or focus the radiation as desired.

Figure 2:
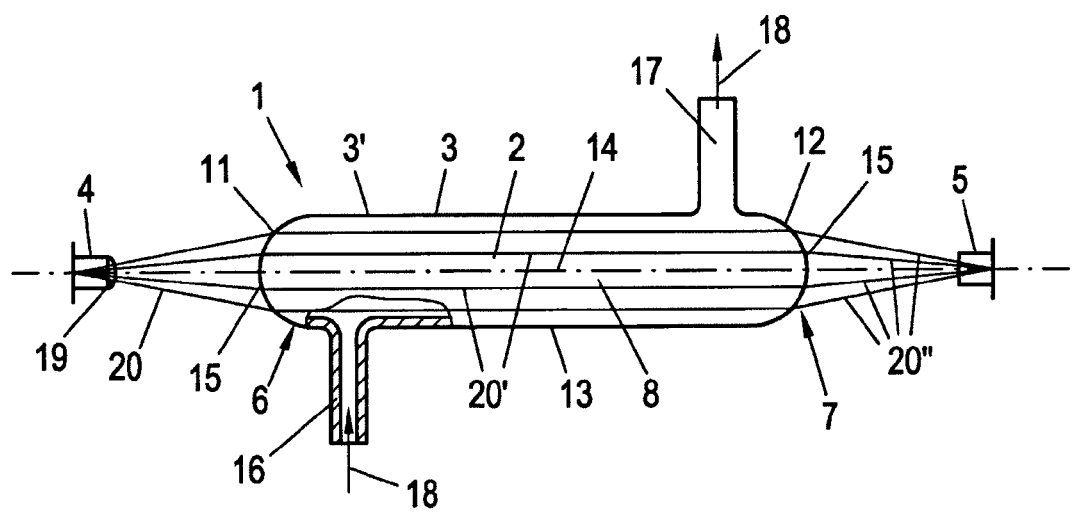
FIG. 2 shows a view of a device for photometric or spectrometric examinations, which is constructed according to a first embodiment of the invention as a flow through cuvette through which radiation passes in the longitudinal direction, comprising convexly curved end surfaces.

In contrast, cuvette 3 of a first embodiment of the invention, as depicted in FIG. 2, has an inlet section 6 with a convexly curved inlet surface 11, which focuses the incident radiation impinging upon the convex inlet surface 11 in the manner of a converging lens. Correspondingly, the outlet section 7 of cuvette 3 has a convexly curved outlet surface 12 in order to focus the transmitted radiation as it is coupled out from the cuvette 3. The curvature of the inlet surface 11 and/or the outlet surface 12 is convex with respect to the inner cavity of cuvette 3, relative to which the inlet surface 11 and/or outlet surface 12 are curved outwardly. The convexly curved inlet surface 11 and/or outlet surface 12 thus focus the radiation impinging upon the respective surface, reducing the fanning out of the beam bundle. Thus, cuvette 3 directly takes over the tasks of an optical system, which was formed by separate optical components in earlier devices 1. The beam formation is thus accomplished by the convexly curved inlet surface 11 and/or outlet surface 12, which are integrated into cuvette 3 so that a compact photometric device 1 is made available without the need for elaborate installations and adjustments plus costly additional optical components. This is particularly advantageous for applications involving excitation radiation in the ultraviolet (UV) or infrared (IR) ranges, as these require special glasses which are elaborate and expensive to produce.

Cuvette 3, depicted in FIG. 2, is shaped as a longitudinal, substantially cylindrical liquid cell 13, through which radiation passes along its longitudinal axis 14. This cuvette 3 displays two end surfaces 15 arranged transversely to its longitudinal axis 14; these are convexly curved inlet surface 11 and convexly curved outlet surface 12. Cuvette 3 is configured as a flow through cuvette 3', equipped with a supply line 16 to introduce liquid sample 2 into liquid cell 13. The cuvette 3 is also equipped with a discharge line 17 to discharge examined liquid sample 2 from liquid cell 13. The flow through cuvette 3' enables continuous examination of the chemical parameters of liquid sample 2. As is further apparent from FIG. 2, liquid sample 2 is introduced into the liquid cell 13 in arrow direction from below with respect to the operating position of cuvette 3 and is discharged, after having passed through liquid cell 13, upwardly through discharge line 17. This configuration considerably reduces the formation of air inclusions, which would hamper examination of liquid sample 2. For this purpose, the embodiment provides, in particular, for the discharge line 17 to be connected to the flow through cuvette 3' at the uppermost position with respect to the operating position of the cuvette.

Radiation source 4, which is expediently configured as a cost effective light emitting diode (LED) 19 for a whole range of wavelengths, produces a divergent beam bundle 20, which is focused into a substantially parallel beam bundle 20' by means of the convexly curved inlet surface 11. In this way, excitation radiation passes through a substantially larger sample volume 8 than in conventional configurations. After having passed through sample volume 8, the substantially parallel beam bundle 20' is concentrated by means of the convexly curved outlet surface 12, into a convergent beam bundle 20'', which is focused on the sensor surface of radiation detector 5. Accordingly, the excitation radiation is used very efficiently and essentially the entire content of the liquid cell 13 is measured as a sample volume 8.

Figure 3:
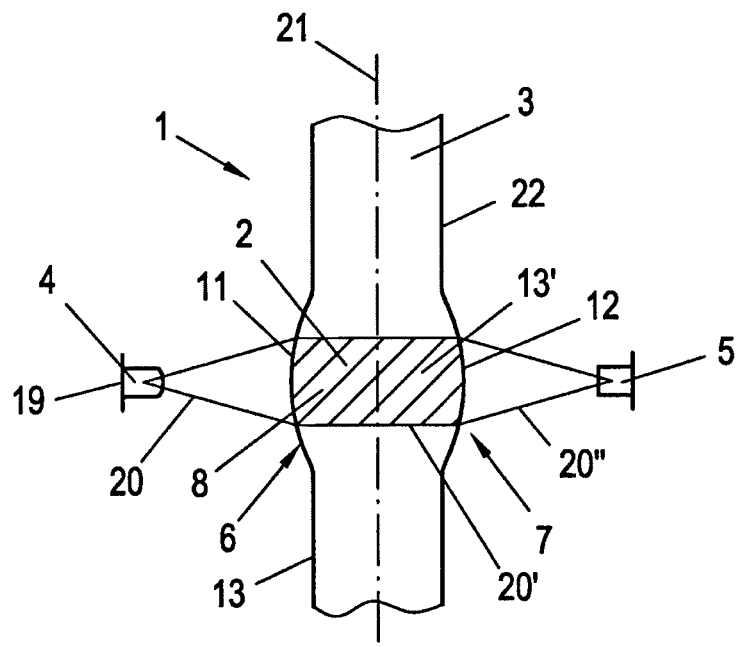
FIG. 3 shows a view of a device for photometric or spectrometric examinations with a cuvette, through which, according to another embodiment of the invention, radiation passes in the transverse direction, wherein the convexly curved inlet and/or outlet window are formed on the lateral surfaces of the cuvette.

FIG. 3 shows an alternative embodiment of device 1, wherein cuvette 3 displays a liquid cell 13' through which radiation passes essentially transversely to the cell's longitudinal axis 21. Liquid cell 13' may be of cylindrical or generally rectangular shape. Depending on the application, cuvette 3 may be configured as a flow through cuvette 3' or as a cuvette into which the reagent is introduced prior to examination. Each of the convexly curved surfaces, inlet surface 11 and outlet surface 12, is formed on a lateral surface 22 of the cuvette 3. In this embodiment, too, the convexly curved inlet surface 11 and outlet surface 12 produce the effect of a converging lens, particularly of a biconvex converging lens, so that, by means of cuvette 3, useful imaging of the excitation radiation is obtained.

Figure 4:
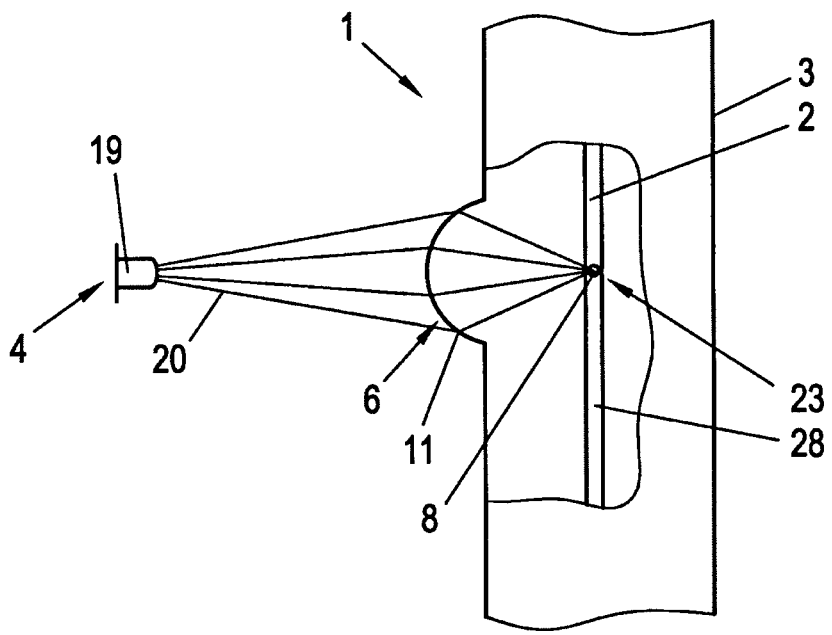
FIG. 4 shows a view of a device for photometric or spectrometric examinations with a cuvette, which, according to a further embodiment of the invention, focuses excitation radiation into a small focal area by means of a convexly curved inlet window.

In FIG. 4, another embodiment of device 1 according to the invention is shown, wherein cuvette 3 displays a stronger convex curvature compared to the previously mentioned exemplary embodiments. Here, the divergent excitation radiation is directly focused into a convergent beam bundle directly on being coupled into cuvette 3; this bundle has a comparably small focal area 23 in the sample volume 8. This embodiment enables very high energy density to be transferred to the sample volume 8. This is of advantage in that a comparably cost effective light emitting diode 19 may be used as a radiation source 4 instead of a typically employed laser.

Figure 5:
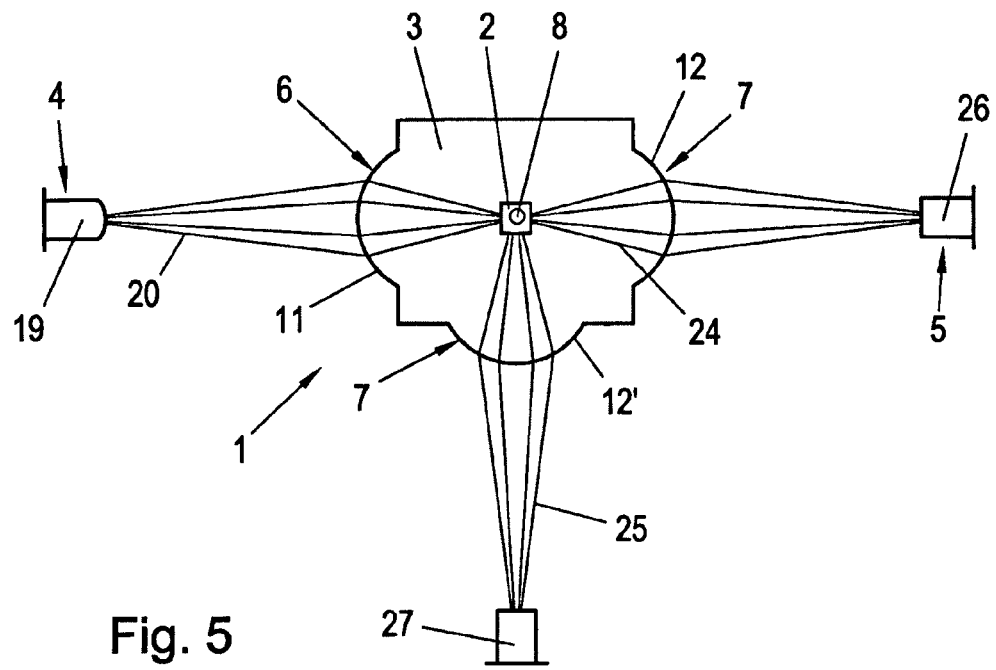
FIG. 5 shows a view of a device for photometric or spectrometric examinations, of the kind used in flow through cytometry, wherein the cuvette, which is designed according to another embodiment of the invention, exhibits two convexly curved outlet windows for coupling out the forward scatter light and the sideward scatter light.

Finally, in FIG. 5, an embodiment of device 1 corresponding to the embodiment of FIG. 4 is shown, wherein a second convexly curved outlet window 12' arranged substantially perpendicular to the inlet surface 11 and/or outlet surface 12 is provided. This embodiment of cuvette 3 enables analytical procedures to be conducted in the manner of flow through cytometry. A forwardly scattered beam bundle, i.e. forward scatter light 24, is coupled out via outlet surface 12 and is detected by a forward scatter light detector 26. Additionally, a beam bundle scattered sidewards, i.e. sideward scatter light 25, is coupled out via outlet surface 12' and is detected by a sideward scatter light detector 27. Flow through cytometry is used to examine cell suspensions, for example, which are directed in a thin spurt through channel 28 of cuvette 3 (comp. also FIG. 4). In an alternative embodiment (not shown), cuvette 3 may have a substantially circular cross section. In addition, cuvette 3 may display at least a third outlet window (not shown), which preferably is arranged opposite to outlet window 12'. A further sideward scatter light detector may be configured with the third outlet window, which detects transversely scattered sideward scatter light, just as sideward scatter light detector 27 does.

The radius of curvature of the convexly curved inlet surface 11 and/or outlet surface 12 has to be adapted to the desired focusing of the excitation radiation or the transmitted radiation, depending on the application. With respect to cost effective production, spherically curved inlet surface(s) 11 and/or outlet surface(s) 12, 12' are appropriate. In applications with high demands on imaging accuracy it may be favorable to configure the inlet surface 11 and/or outlet surface(s) 12, 12' in the form of spherical surfaces in order to avoid lens errors.

FIGS. 6 and 7 show a longitudinal and a cross-sectional view of a flow through cuvette 3' respectively, which features a favorable configuration of supply line 16 and discharge line 17 with respect to the flow conditions within liquid cell 13. As is evident from FIG. 6, both, a longitudinal axis 16' of supply line 16 and a longitudinal axis 17' of discharge line 17 are inclined relative to the longitudinal axis 14 of liquid cell 13. As is evident from FIG. 7, both the longitudinal axis 16' of supply line 16 and the longitudinal axis 17' of discharge line 17 are furthermore arranged at an inclination angle with respect to a transverse axis 29 of liquid cell 13. In this embodiment, liquid sample 2 is supplied to and discharged from liquid cell 13 essentially tangentially, thereby achieving better blending of liquid sample 2 and reduced turbulence in the liquid flow.

In FIG. 8, an alternative embodiment of flow through cuvette 3' is shown, wherein supply line 16 and discharge line 17 each comprise two portions 16a, 16b and 17a, 17b respectively, having different cross sectional areas. Accordingly, supply line 16 has a portion 16a running in the direction of the longitudinal axis 14 of liquid cell 13 and ending in a portion 16b aligned at right angles to it. This latter portion, though which liquid sample 2 is supplied to liquid cell 13, has a larger cross-section than portion 16a. Portion 17b of discharge line 17, which follows on liquid cell 13, is cross sectionally larger than the downstream portion 17a of discharge line 17, onto which portion 17b of discharge line 17 adjoins in longitudinal direction.

Figure 9:
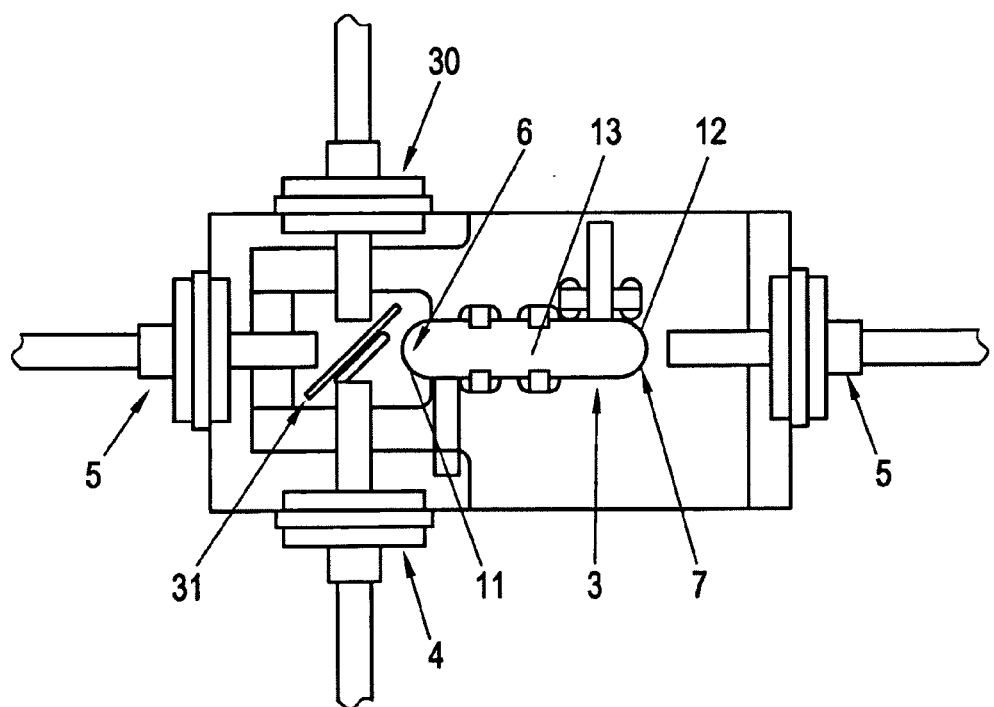
FIG. 9 shows a view of a configuration for photometric or spectrometric examinations, comprising a dichroic mirror and a reference sensor.

In FIG. 9, a configuration for conducting photometric or spectrometric examinations is shown schematically, comprising a cuvette 3 which contains liquid sample 2, a radiation source 4 and two separate radiation detectors 5, which detect different or complementary interactions of coupled in radiation with liquid sample 2. Additionally, a reference sensor 30 is provided for calibrating the measuring signal. In the configuration shown in FIG. 9, a dichroic mirror 31 is provided for dividing the radiation emitted by radiation source 4, which mirror reflects a part of the light spectrum into the direction of inlet section 6 and lets the other wavelength ranges through.

In FIG. 10, an alternative configuration for conducting photometric or spectrometric examinations is shown, which provides for a translucent mirror 32 instead of the dichroic mirror 31 shown in FIG. 9, which directs a part of the radiation emitted by radiation source 4 to reference sensor 30 while the transmitted part of the radiation impinges upon the convexly curved end surface 15 of inlet section 6. To detect the radiation interacting with liquid sample 2, radiation detectors 5 are arranged in the areas of inlet section 6 and outlet section 7.

The invention claimed is:
1. A device for photometrically or spectrometrically examining a liquid sample, comprising a cuvette, which can be arranged in the beam path between a radiation source and a radiation detector and which accommodates the liquid sample to be examined, a radiolucent inlet section for coupling in radiation produced by means of the radiation source, which radiation interacts with a sample volume, and a radiolucent outlet section for coupling out radiation intended to be detected in the radiation detector, wherein the inlet section has an inlet surface essentially spherically convexly curved in such a way and the outlet section of said cuvette has an outlet surface essentially spherically convexly curved in such a way that the incident radiation is focused in the manner of a converging lens, the inlet surface and the outlet surface being integrally formed with a portion of the cuvette containing the liquid sample, wherein the radiation illuminated directly at the inlet surface is divergent at the inlet surface.

2. The device according to claim 1, characterized in that the cuvette comprises a liquid cell through which radiation passes essentially along the cell's longitudinal axis and which is of a substantially cylindrical shape, wherein an end surface of the liquid cell is shaped as a convexly curved inlet surface and outlet surface.

3. The device according to claim 1, characterized in that the cuvette comprises a liquid cell through which radiation passes essentially in a direction transverse to the cell's longitudinal axis and which is of a substantially cylindrical shape, wherein the convexly curved inlet surface and outlet surface are provided on the lateral surfaces of said cuvette.

4. The device according to claim 1, characterized in that the cuvette is configured as a flow through cuvette, which has a supply line and a discharge line for the liquid sample to be examined.

5. The device according to claim 4, characterized in that, with respect to the operating position of the cuvette, the supply line is connected to the cuvette vertically below the discharge line, wherein the discharge line is connected to an upper-side section of the cuvette.

6. The device according to claim 4, characterized in that a longitudinal axis of the supply line and a longitudinal axis of the discharge line are inclined relative to a longitudinal axis and a transverse axis of the flow through cuvette.

7. The device according to claim 4, characterized in that the supply line and the discharge line comprise portions having different cross-sectional areas.

8. The device according to claim 1, characterized in that the cuvette has at least one convexly curved outlet surface for a forwardly focused beam bundle and a further convexly curved outlet surface for a transversely focused beam bundle.

9. The device according to claim 1, comprising a radiation source configured to produce a divergent beam bundle, which is a light emitting diode, and a radiation detector, which is a CCD sensor.

10. The device according to claim 9, characterized in that a reference sensor is provided for calibrating the radiation detector.

11. The device according to claim 1, characterized in that a stirring device is provided for stirring the liquid sample.

12. The device according to claim 1, characterized in that the convexly curved inlet surface focuses a divergent beam bundle into a substantially parallel beam bundle, which, after having passed through the sample volume, is focused into a convergent beam bundle by means of the convexly curved outlet surface, which latter bundle is detectable by the radiation detector.

13. The device according to claim 1, characterized in that the inlet surface of the cuvette is curved in such a way that radiation impinging upon the inlet surface is focused within a relatively narrow focal area of the liquid sample.

14. A method for photometrically or spectrometrically examining a liquid sample, comprising the steps of:
  i) arranging a cuvette accommodating the liquid sample to be examined in a beam path between a radiation source and a radiation detector,
  ii) coupling in a radiation produced by means of the radiation source through a radiolucent inlet section of the cuvette,
  iii) coupling out the radiation through a radiolucent outlet section of the cuvette, the inlet section of the cuvette having an inlet surface essentially spherically convexly curved in such a way and the outlet section of said cuvette having an outlet surface essentially spherically convexly curved in such a way that the incident radiation is focused in the manner of a converging lens, the inlet surface and the outlet surface being integrally formed with a portion of the cuvette containing the liquid sample, wherein the radiation illuminated directly at the inlet surface is divergent at the inlet surface.

* * * * *